United States Patent [19]

Seifert, deceased et al.

[11] Patent Number: 4,468,372

[45] Date of Patent: Aug. 28, 1984

[54] HYGIENIC AIR PURIFYING DEVICE

[75] Inventors: Reuben E. Seifert, deceased, late of Orlando, Fla., by Frances Seifert, administratrix; Jakob Harich, 31 S. Cortez Ave., Winter Springs, Fla. 32803

[73] Assignee: Jakob Harich, Winter Springs, Fla.

[21] Appl. No.: 307,142

[22] Filed: Sep. 30, 1981

Related U.S. Application Data

[63] Continuation-in-part of Ser. No. 132,028, Mar. 20, 1980, abandoned.

[51] Int. Cl.³ ............................ A61L 9/12; A61L 9/22
[52] U.S. Cl. ...................................... 422/124; 55/122; 55/138; 55/279; 422/4; 422/121
[58] Field of Search .................. 422/4, 122, 124, 121, 422/120; 55/122, 138, 279

[56] References Cited

U.S. PATENT DOCUMENTS

| | | | |
|---|---|---|---|
| 3,017,239 | 1/1962 | Rodman | 55/279 X |
| 3,744,216 | 7/1973 | Halloran | 422/124 X |
| 3,782,905 | 1/1974 | Huang et al. | 422/121 |
| 3,958,959 | 5/1976 | Cohen et al. | 55/122 X |
| 4,049,400 | 9/1977 | Bennett et al. | 422/4 X |
| 4,102,654 | 7/1978 | Pellin | 55/138 X |
| 4,244,710 | 1/1981 | Burger | 422/4 X |

Primary Examiner—Barry S. Richman

[57] ABSTRACT

A fan draws an air stream or path, contaminated with bacteria, fungi, or viruses into a hygienic treatment device. The device includes a perforated cartridge initially confronting the air stream and carrying a plurality of silicate pellets therein. The pellets are impregnated with a germicidal agent before emplacement in the cartridge. A stack of parallel, spaced plates separated by phenolic wafers are positioned closely adjacent and slightly downstream from the cartridge. A voltage of at least 4,000 volts is supplied to the stack of metallic plates. The moving air stream generates a siphoning action on the pellets to better withdraw the germicidal agent therefrom. The germicidal agent, which is preferably a grapefruit seed extract, destroys the bacteria, fungi, and viruses, and causes airborne particles to become positively charged. The contaminated airborne particles are then collected by the negatively charged plates in the stack.

5 Claims, 4 Drawing Figures

HYGIENIC AIR PURIFYING DEVICE

This application is a continuation-in-part of Ser. No. 132,028 filed Mar. 20, 1980 and now abandoned.

BACKGROUND OF THE INVENTION

From the early days of Pasteur and Lister, the relationship between infectious organisms and contamination has been well known. There have been many attempts to sterilize or purify environments to prevent contamination of people, food, and articles, otherwise clean from infection, by airborne bacteria, fungi and viruses. There have been many approaches to providing clean, sterile atmospheres.

Systems for delivering aseptic air to and over patients in hospitals are suggested by U.S. Pat. Nos. 3,294,480 and 3,239,305, each invented by Potapenko, U.S. Pat. No. 3,267,955 to Logan et al, and U.S. Pat. No. 3,721,067 to Agnew. Another improvement in hospital room arrangements is suggested in U.S. Pat. No. 3,158,457 to Whitfield which suggests the circulation of large amounts of air.

Another approach to the collection and removal of airborne bacteria, viruses, fungi, and the like from environments is illustrated and described in U.S. Pat. No. 2,825,102 to Hicks et al in which an electric field in an air flow path is used to direct airborne particles to an incinerator.

There are many patents and publications directed to air purification processes in which the air is merely drawn over or subjected to a germicidal agent of one type or another. Examples of such types of processes include U.S. Pat. No. 3,340,680 to Fields et al which is directed to the removal of bacteria and viruses from air by subjecting the air with a small but effective quantity of a polymeric hydrophilic polyelectrolyte. Similarly, in the U.S. Pat. No. 3,433,578 there is disclosed the process of purifying air by washing it with a mixture of water, polyhydroxy alcohol, and glycol ether. Another patent exemplary of this type of approach is U.S. Pat. No. 3,385,654 to Yardney et al in which the contaminated air is contacted by an antimicrobial metal compound which is the silver salt of a lower fatty acid. Other examples of germicidal compositions in the prior art include glycols, ozone, hydrogen peroxide, potassium permanganate, carbon bisulfide, naptha, benzene, and oil of eucalyptus. These compositions may be utilized either as a vapor or as a wash.

One final approach is shown and described in U.S. Pat. No. 4,035,451 to Tringali which is directed to a cartridge type system which induces an air flow past a germicidal product capable of being vaporized. The cartridge includes a hollow, apertured container with a fan therein, a battery for driving the fan, and a support for a strip material having a convoluted configuration mounted in the container. A quantity of germicidal product is impregnated in the strip material.

While all of the above types of devices and compositions may be effective to a certain extent, all of them also suffer certain disadvantages. For example, the large laminar-flow type air changing systems require extensive air treatment equipment. Also, the compositions alone are effective against an air stream passing thereover or therethrough; however, the germicidal agent must be continuously changed with the result that the use thereof is relatively expensive and troublesome. Additionally, where a contaminated air stream is passed over or through a germicidal agent, airborne particles still manage to pass through the treatment and get back into and contaminate the controlled environment. The cartridge of Tringali may be effective but only to a very minimum extent, it is very slow in changing the air of a room, and it requires direct contact between the air and the strip material into which the germicidal product is impregnated to be effective.

SUMMARY OF THE PRESENT INVENTION

The present invention, on the other hand, is directed to a portable unit which may be set in an enclosed room, plugged in to a conventional 110 volt AC outlet, and utilized to provide a biomedically clean room. The hygienic air unit according to the present invention not only neutralizes bacteria, fungi, and viruses present in the air, but also eliminates airborne particles which are considered to be sources of cross-contamination and of secondary infections. The device according to the present invention is useful for doctors', dentists', and veterinarians' offices and consulting rooms as well as hospitals, health institutions, schools, restaurants, hotels, motels, and any other areas where infection is likely to be transferred. Also, the device is useful in cheese, meat, and food processing plants, as well as greenhouses, to prevent contamination of clean food and plants by airborne micro-organisms and related fungi cultures.

In general, the device and method according to the present invention operate on the concept that passing the contaminated air across a plurality of silicate pellets treated with a germicidal agent, followed by electromagnetic collection of charged airborne particles will serve to more efficiently eliminate germs and micro-organisms and maintain a clean, healthy atmosphere in the environment in which the device is placed.

The silicate pellets are preferably carried by a cartridge of some type which may be a perforated cylindrical tube or a perforated plate, either of which contain the pellets in compartments therein and cause the air stream to be passed thereover or in close proximity thereto. The pellets may be treated with any of a number of different types of germicidal agents, as long as the agent is compatible with the electromagnetic collection means (the agent provides positive charge on airborne particles) and does not deposit any type of insulating or oily scum thereover. For example, the preferred antimicrobial agent which has been successfully used is a grapefruit seed extract, more formally identified as FDA registered number FDS CRMCS No. 1R0013919.

As far as the means for generating the electromagnetic collector is concerned there is provided a stack of spaced, phenolic-coated metallic plates separated by dielectric insulating wafers or washers and connected to a strong voltage source (at least 4,000 volts). The relationship between the number and size of the plates used and the amount of voltage provided is such that the voltage is sufficient to generate a negative charge on the plates which will attract the positively charged airborne particles. The movement of air at a rate of 45–50 cubic feet per minute provides a siphoning effect on the germicidal agent in the adjacent silicate pellets. The result is that the discharge of the germicidal agent will be much more effective than that achieved by merely passing the air over the germicidal agent or through a spray thereof. Additionally, the stack of negatively charged plates collects the positively charged airborne particles and prevents their re-entry into the atmosphere of the room being cleaned.

The aforementioned design is therefore easily susceptible to being encased in a portable unit with dimensions no larger than a portable typewriter case or attache case.

It is therefore an object of the present invention to provide a portable, effective, hygienic air purification unit.

It is another object of the present invention to provide an air purifying apparatus of the type described in which the efficacy of germicidally treated pellets may be improved.

It is still another object of the present invention to provide an air purifying apparatus of the type described in which an electromagnetic field collects germicidally treated airborne particles.

Other objects and a fuller understanding of the invention will become apparent upon reading the following detailed description of a preferred embodiment along with the accompanying drawings in which.

DETAILED DESCRIPTION OF A PREFERRED EMBODIMENT

Figure 1:
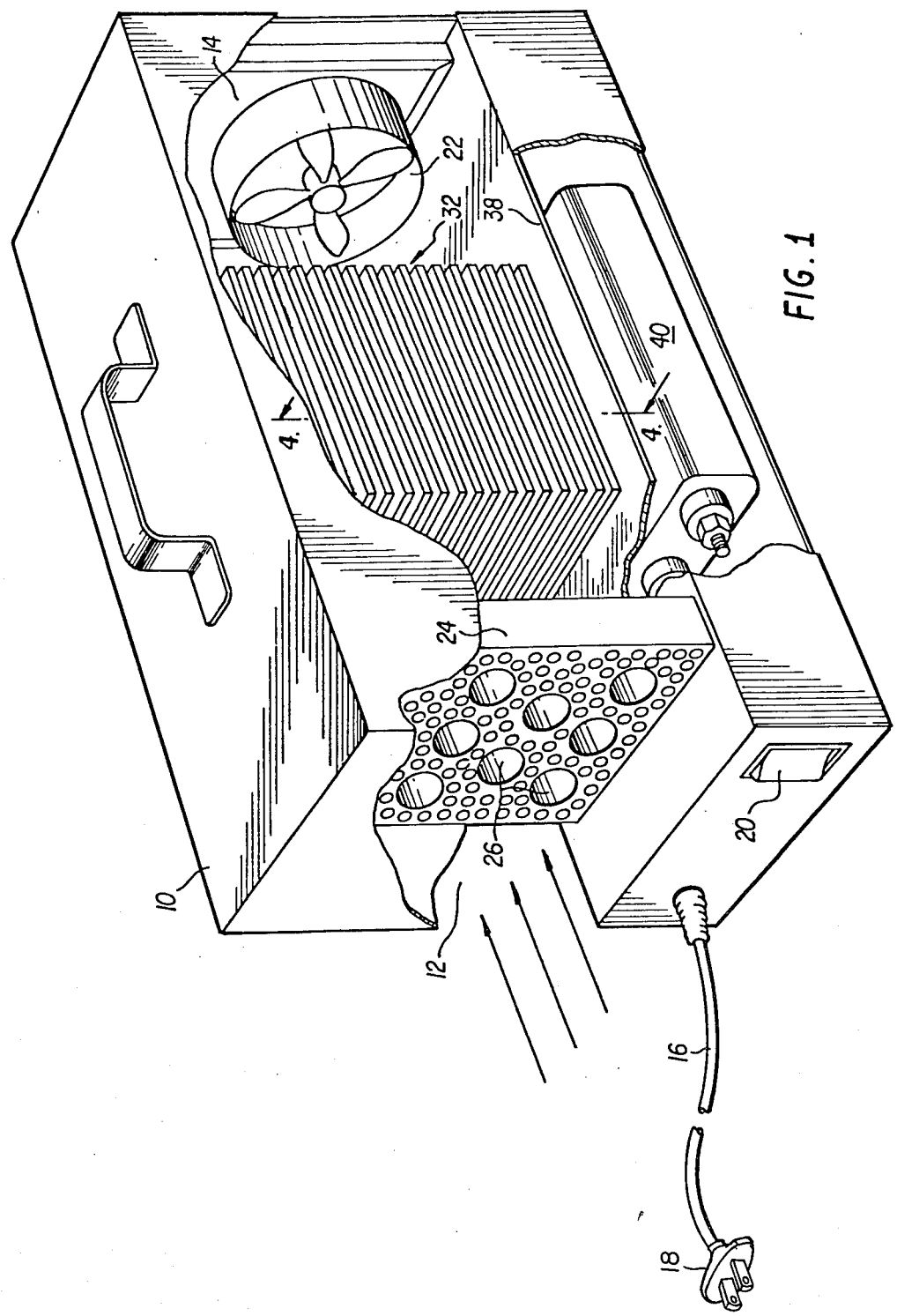
FIG. 1 is a perspective view with parts broken away, illustrating the portable unit according to the present invention.
Figure 2:
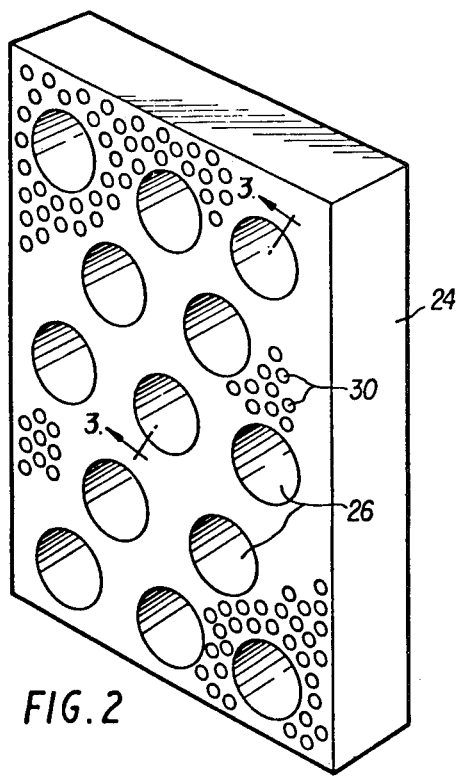
FIG. 2 is a perspective view illustrating the cartridge removed from the enclosure.

Turning now to the embodiment illustrated in the drawing, the hygienic air purifying device according to the present invention includes an enclosure 10 having an air inlet 12 at one end and an air outlet 14 at the other end. A cord 16 having a plug 18 at the free end thereof connects the apparatus to a source of 110-120 volts AC power. Power to the unit is controlled by an on-off switch 20.

A fan 22 is mounted at one end of the enclosure 10, preferably the rear end 14, and is connected to the incoming source of power through line 16. Fan 22 draws air through the inlet 12, causing it to pass out through the outlet 14, thus generating the required air flow path through the unit.

Figure 3:
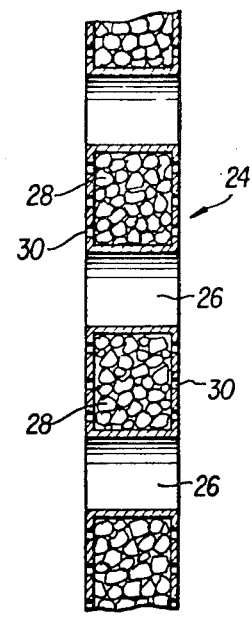
FIG. 3 is a cross-sectional view taken substantially along lines 3—3 in FIG. 2.
Figure 4:
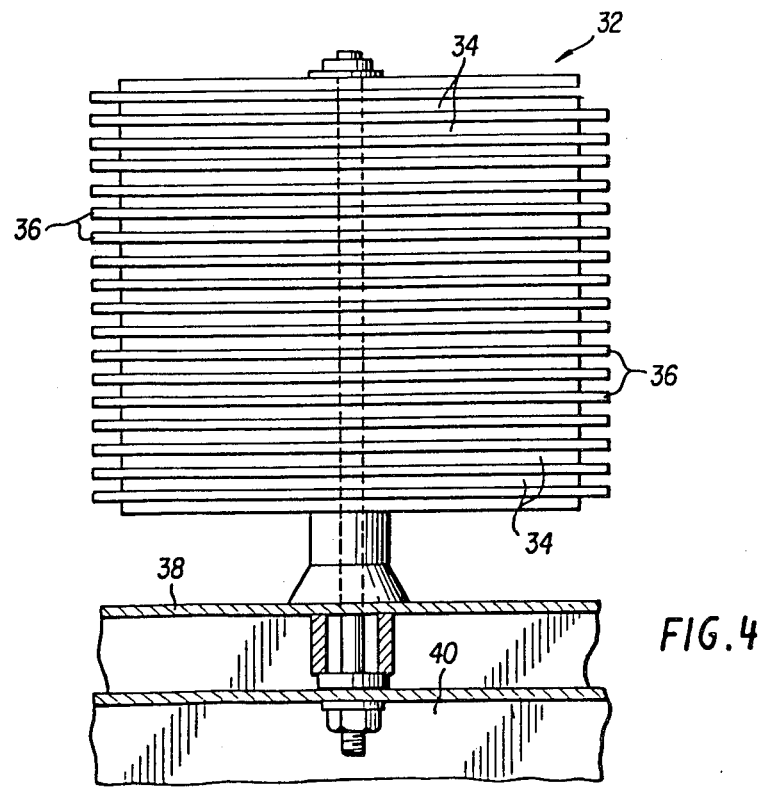
FIG. 4 is a cross-sectional view taken substantially along lines 4—4 in FIG. 1.

A cartridge 24 is mounted in the air flow path and contains a plurality of openings 26 therein for allowing passage of air therethrough. Within the walls of cartridge 24 are retained a plurality of silicate pellets 28 (FIG. 3), the vapors of which are allowed to escape to the atmosphere surrounding openings 26 through minute or smaller openings 30 in the wall of cartridge 24. The silicate pellets 28 are impregnated with a germicidal or antimicrobial agent. Such agent may be selected from many different types, the only requirement being that the agent be compatible with the stacked plates which will be described hereinafter. The term "compatible" means here that the agent will provide a charge on the airborne particles opposite in polarity to that of the charge applied to the stack of plates, and will not damage or coat the plates which would tend to nullify the charge. A preferred antimicrobial agent is FDA CRMCS No. 1R0013919. If desired, an electronic indicator (not shown) may be attached to the silicate cartridge 24 to signal that the amount of chemical in the pellets has been used up and to indicate the need of a new cartridge.

In FIG. 4, there is illustrated a collector means 32, which is negatively charged, closely adjacent and slightly downstream from the pellets 30. The collector means 32 is formed of a plurality of stacked, spaced metallic (aluminum) plates 34, each of which is coated with approximately a 5 mil. layer of phenolic resin to inhibit the production of ozone. A dielectric wafer or washer 36 separates each pair of adjacent plates. Various dielectric materials might be used for wafers 36 but phenol is known to function satisfactorily. The stack of plates is secured to a platform or plate 38 close to the bottom of the unit 10. A transformer 40 is suspended from plate 38 and serves to convert the 110 volt AC input to a considerably higher voltage sufficient to negatively charge plates 34. Preferably, the secondary winding of the transformer is such that at least 4,000 volts are provided to the stack of plates 34.

As the contaminated air enters the unit, it passes by and through the cartridge 24 containing the germicidally treated silicate pellets 28. The movement of the air causes the germicidal agent to be siphoned out of the pellets and enter the air stream. In the air stream, the germicidal agent serves to kill the bacteria, fungi, and viruses therein as well as to positively charge the airborne particles. Further, the negatively charged plates 34 act as a collector to entrain the airborne particles thereon so that they cannot be retransmitted to the atmosphere. Therefore the unit serves not only to kill the bacteria, fungi, and viruses passing therethrough, but also to prevent airborne particles from re-entering the environment. To the knowledge of the inventors, this combination of effects has not been accomplished before this invention.

Various changes are possible in the embodiment shown and described hereinabove. For example, while a comb-like cartridge 24 is illustrated in FIG. 2, it is also possible that the cartridge be a plastic tube containing the pellets with openings therethrough, as the shape of the cartridge is not critical. Further, the shape of the stacked plates may be square, rectangular, or round, even though rectangular plates have been selected for the preferred embodiment. Depending on the size of the area to be cleaned, the size of the unit as well as the size of the voltage source may vary. The unit described hereinabove has been found effective for rooms of 15,000 cubic feet and will satisfactorily operate to completely circulate and clean the air in the room every five hours. The fan for such unit is such as will move forty-five to fifty cubic feet of air per minute through the enclosure 10.

Various tests have been conducted with the unit to determine its efficacy. For example:

I. GERMICIDAL AGENT ALONE WITH NO ELECTRIC FIELD

A closed room approximately 15,000 cubic feet was selected, doors and windows were tightly sealed. A 1–1000 Hyamine solution was prepared in water dissolved for disinfecting. All surface areas were thoroughly washed; floor, walls and ceiling. After a 24-hour period, nutrient and Sab. contact agar plates were used and contact was made from the disinfected room, floor, walls and ceiling. All contact plates were incubated for 24–30 hours at a temperature of 37° C. for bacterial growth, and for fungi 35° C. with a relative humidity of 85–90%. After the required incubation period as described, the plates were examined, a few colonies from the floor areas in the nutrient was developed and a few fungi sporolation in the Sab. agar contact in the 30-hour period. These are most common airborne organisms.

A 48-hour subcultured bacterial organism and seven-day cultured fungi organism were inoculated in their appropriate media in freshly prepared nutrient and Souraud's agar plates.

The following micro-organisms were used: three bacterial organisms were from the Florida Hospital, these three organisms are chemically resistant to various disinfectants.

| | | |
|---|---|---|
| 1. | *Escherichia coli* | Florida Hospital |
| 2. | Enteriococci | Florida Hospital |
| 3. | Pseudomonas | Florida Hospital |
| 4. | *Staph. aureus* | ATCC 6538 |
| 5. | *Streptococcus faecalis* | ATCC 19635 |
| 6. | *Aspergillus niger* | ATCC 6275 |
| 7. | *Pullularia pullulans* | ATCC 9348 |

Each culture was prepared in 12 plates and exposed at various levels in the testing room. All inoculated plates were openly exposed on the floor and three feet off the ground floor on cabinets.

A heating unit was installed with a thermostat control at 37° C. and relative humidity of 85–90%. The air unit without the dielectric plates were set in operation, the fan was operating on 110 v by an air flow 57–63 cubic feet per minute, by the input and output air flow system.

The experimental exposure room was tightly sealed during the exposure period. From each exposed organism two inoculated plates were incubated for and served for control.

| | Bacterial Results After 48 Hours In The Exposure Room, and Incubation Results | | |
|---|---|---|---|
| Organisms | Florida Hospital | 24 Hrs. | 48 Hrs. |
| *E. coli* | " | + | +++ |
| Enteriococci | " | ++ | +++ |
| Pseudomonas | " | ++ | +++ |
| *Staph. aureus* | " | ++ | +++ |
| *Strep. faecalis* | " | ++ | +++ |
| Control incubator | | +++ | +++ |

Symbol
+ slight growth
++ moderate growth
+++ heavy over-growth

The bacterial plates with growth were removed from the test room and carefully examined and destroyed chemically and with heat temperature. Plates in direct air flow contact from the unit in the first 24 hours showed only moderate growth development, 48 hours later heavy over growth developed. The inoculated fungi culture were exposed for a period of seven days.

| Fungi Results After 7 Days' Exposure and Control Under Incubation | | |
|---|---|---|
| Fungi Culture | 4 Days | 7 Days |
| *Asper. niger* | ++ | +++ |
| Pull. pull. | ++ | +++ |
| Control | ++ | +++ |

Symbol
++ moderate growth
+++ heavy over-growth

The air unit was tested by removing the dielectric plates, only with the treated silicate pellets and four-inch electric fan. The exposed organisms and fungi culture reduced the growth bacteria in the first 24-hour exposure compared to control incubation, but heavy growth in 48 hours where the sporilation of the fungi culture in the first four days was somewhat slower compared to control under incubation, but heavy overgrowth in seven days. There was no significant difference between control and exposure.

| Results After 48 Hours' Exposure Air Unit Circulation-Dielectric Plates Alone | | |
|---|---|---|
| Test Organism | 24 Hr. Exposure | 48 Hr. Exposure |
| *Staphylococcus aureus* | + | ++ |
| *Psudomonas earuginosa* | ++ | +++ |
| *Escherichia coli* | ++ | +++ |
| Enteriococci | +++ | +++ |
| *Streptococcus faecalis* | ++ | +++ |

Symbol
+ slight growth
++ moderate growth
+++ heavy growth
Control
+++ heavy growth The growth developed slowly in the first 18 hours in the exposed room and increased after 24 hours' exposure.

Heavy growth developed in 48 hours. Ozone produced showed no effect on the test organisms, specifically on *Pseudomonas earuginosa*, *Escherichia coli*, and Enteriococci; all three organisms being drug resistant and a major problem in hospitals.

Test on Swiss Mice

One hundred Swiss mice, 18–21 grams, and 20 guinea pigs were exposed under the ozone air circulating unit in the identical room of 15,000 cubic feet, for 120 hours total for five days. Laboratory feed and tap water were supplied daily. Close observation was kept daily. The water consumption increased in the first 24 hours, between 15–19%, with a decrease of food utilization of approximately 10–12%. At the end of each 24-hour period, the dead animals were counted and removed.

| Results After 120 Hours' Exposure Mice and Guinea Pigs | | | | | | | |
|---|---|---|---|---|---|---|---|
| Animals | | | | | | | |
| Swiss Mice - 100 Hours of Exposure | | | | | | | |
| 24 | 48 | 72 | 96 | 120 | Female Dead | Male Dead | Total Dead |
| 0 | 0 | 5 | 9 | 14 | 16 | 12 | 28 |
| Guinea Pigs - 20 Hours of Exposure | | | | | | | |
| 24 | 48 | 72 | 96 | 120 | Female Dead | Male Dead | Total Dead |
| 0 | 0 | 1 | 3 | 5 | 6 | 3 | 9 |

Toxic signs were respiratory depression, nasal discharge and dyspnea. All animals were sacrificed by inhalation of chloroform. Necropsies were performed; there were no significant changes with the exception of lung congestion in both animal groups.

Histopathological examination of tissues revealed nonspecific inflammatory changes in control animals. Inflammatory changes in exposed animals were noted in the lungs, liver and kidneys of the majority of the exposed animals and varying degrees of pneumonitis, edema and emphysema in the lungs.

II. COMBINATION OF GERMICIDAL AGENT PLUS ELECTRIC FIELD

A comparative study with the air circulation unit of the invention was performed under the same conditions and exposure methods as set forth hereinabove. Five organisms previously subcultured were used for this test:

| 1. Staphylococcus aureus | ATCC 6538 |
| 2. Pseudomonas earuginosa | ATCC 10145 |
| 3. Escherichia coli | FDA PC 1508 |
| 4. Enteriococci Florida Hospital | |
| 5. Streptococcus faecalis | ATCC 19635 |

The 48-hour test organisms were inoculated in freshly prepared Nutrient agar plates. Each organism was carried in 50 petri dishes containing 20 ml. of media, a total of 250 plates. Inoculated plates from each organism were set on the floor, and three feet above the floor. Ten to twelve inches distance from each exposed test organism were five plates inoculated from each organism for control and incubated at 37° C. for 48 hours, to compare with exposed plates. The exposed plates in the 15,000 cubic foot room had an identical temperature (37° C.) as compared to control incubation. The inoculated test plates were uncovered for a 48-hour exposure. After 24 hours' exposure under the air circulation unit of the present invention, only Enteriococci and *Pseudomonas earuginosa* plates set on the floor had a few growth noted.

| Results After 48 Hours' Exposure New Air Circulation Unit | | |
|---|---|---|
| Test Organism | 24-Hr. Exposure | 48-Hr. Exposure |
| Staphylococcus aureus | − | − |
| Pseudomonas earuginosa | + | + |
| Escherichia coli | − | − |
| Enteriococci | + | + |
| Streptococcus Faecalis | − | − |

Symbol
+ slight growth
− no growth
Control Plates
+++ heavy growth

The slight growth developed in plates set on the floor, *Pseudomonas earuginosa* and Enteriococci, the organisms were inhibited from a continuous growth development. All exposed test organism plates were compared to control plates incubated, where full growth developed.

The slight growth developed during the first 24-hour exposure by *Pseudomonas earuginosa* and Enteriococci were transferred with a sterile, 4 mm platinum loop, inoculated in freshly prepared Nutrient agar plates, and incubated at 37° C. for 48 hours with control plates. There were six plates from each organism.

III. UNIT WITH ELECTRIC FIELD AND NO GERMICIDAL AGENT

In the following control study, a stack of 20 dielectric plates were mounted in an air circulation unit and connected to the transformer thereof to produce ozone for disinfecting and sterilization with an air flow input and output of 65-70 feet per minute. The unit was exposed in a 15,000 cubic foot room, where doors and windows were tightly sealed for testing. No germicidally treated pellets were used, as the cartridge was removed. Five organisms previously subcultured were used for this test:

| 1. Staphylococcus aureus | ATCC 6538 |
| 2. Pseudomonas earuginosa | ATCC 10145 |
| 3. Escherichia coli | FDA PC 1508 |
| 4. Enteriococci Florida Hospital | |
| 5. Streptococcus faecalis | ATCC 19635 |

The 48-hour test organisms were inoculated in freshly prepared nutrient agar plates. Each type of organism was placed in 50 petri dishes containing 20 ml. of media, a total of 250 plates. The inoculated plates from each organism were set on the floor and three feet above the floor; 10-12 inches in distance from each exposed test organism were 5 plates, inoculated from each organism for control and incubated at 37° C. for 48 hours to compare with exposed plates.

The exposed plates in the 15,000 cubic foot room had identical temperature (37° C.) compared to the control incubator. The inoculated test plates were uncovered for 48 hours' exposure. In the first 24 hours, ozone was developed and detectable by odor in the air, and humidity was reduced to approximately 15-21%. Water was set on electric plates to restore a humidity of 40-45%. After 48 hours' exposure, the inoculated plates from each test organism were examined.

| Results After 48 Hours' Incubation Transferred Organisms From Exposed Air Circulation | | |
|---|---|---|
| | 24-Hr. Exposure | 48-Hr. Exposure |
| Test Organism | | |
| Pseudomonas earuginosa | + | ++ |
| Enteriococci | ++ | +++ |
| Control | | |
| Pseudonomas earuginosa | +++ | +++ |
| Enteriococci | +++ | +++ |

Symbol
+ slight growth
++ moderate growth
+++ heavy growth

There are indications the transferred organisms slowly developed growth in the first 24 hours compared to control; in 48 hours there was moderate growth. The air circulation unit had some effect on the test organisms during the exposure period. Staining method and microscopic examination showed some changes of the cell wall and protoplasma affected from the exposure.

Test on Swiss Mice

One hundred Swiss mice, 18-21 grams, and 20 guinea pigs were exposed under the same conditions as control, with the exception of the use of the air circulation unit of the present invention in the identical room of 15,000 cubic feet for 120 hours, total of five days. Laboratory feed and tap water were supplied daily. Close observation was kept daily of water and food utilization and behavior. During the 120 hours' exposure period, food utilization and water consumption compared to the control group, unexposed was normal. All test animals, after exposure, were sacrificed by inhalation of chloroform.

| Results After 120 Hours' Exposure Mice and Guinea Pigs |
|---|
| Animals |

-continued

Results After 120 Hours' Exposure
Mice and Guinea Pigs

Swiss Mice - 100
Hours of Exposure

| 24 | 48 | 72 | 96 | 120 | Female Dead | Male Dead | Total Dead |
|---|---|---|---|---|---|---|---|
| 0 | 0 | 0 | 0 | 0 | 0 | 0 | 0 |

Guinea Pigs - 20
Hours of Exposure

| 24 | 48 | 72 | 96 | 120 | Female Dead | Male Dead | Total Dead |
|---|---|---|---|---|---|---|---|
| 0 | 0 | 0 | 0 | 0 | 0 | 0 | 0 |

During the exposure period, there were no toxic signs. Necropsies on all test animals were performed and there were no gross pathological alterations compared to control and exposed animals.

Thus, it is demonstrated that the device according to the invention eliminates airborne, harmful micro-organisms, mildew, mold and fungi cultures. The device is applicable for public health and would be useful in health care facilities, hospitals, schools, restaurants, hotels, motels, veterinarian and dental offices and any other facilities where infection is transferred. Further, the device will also be applicable for food, cheese and meat processing plants to prevent contamination by airborne micro-organisms and related fungi cultures. Independent testing has shown that the device is perfectly safe and complies with all federal regulations.

In a different type of environment, that of a greenhouse used for the growing of plants such as orchids and ferns, quite unexpected results were obtained in utilization of the present invention to determine if it would be effective in controlling and/or curing plant diseases such as leaf rot, petal blight, rust, mold and the like. The unexpected result was that not only were the diseases controlled, but significantly increased growth was also observed, along with increased vitality and blooming. These conditions were in addition to the control, and in many instances the elimination of molds, fungus, bacteria and the like. These results were obtained without the use of any fungicides or pesticides. The elimination of the need for such chemicals is an additional unexpected result. Even further, the normal problem of growth of mold or fungus on the walkways and walls of the greenhouses was virtually eliminated, and therewith the necessity for cleaning, repainting or replacing is eliminated.

While a preferred embodiment of the invention has been described in detail, it is apparent that various changes and modifications might be made without departing from the scope of the invention which is set forth in the enclosed claims.

What is claimed is:

1. A hygienic air purifying device for use in cleaning an air stream contaminated with bacteria, fungi, and/or virus, as well as with other airborne particles, said device comprising:
    (a) an enclosure having an air inlet at one end and an air outlet at the other end;
    (b) a fan for creating a path for an air stream through said enclosure;
    (c) a cartridge mounted in said path and having a plurality of openings therein for allowing passage of the air stream therethrough;
    (d) a plurality of pellets carried by said cartridge, said pellets being impregnated with a germicidal agent, said germicidal agent being characterized by both an ability to be siphoned into said air stream and neutralize said bacteria, fungi, and/or viruses and an ability to induce an electrical charge on airborne particles entrained in said air stream; said germicidal agent being the primary source of the electrical charge to said airborne particles;
    (e) collecting means positioned downstream from said pellets, said collecting means having an electrical charge applied thereto, opposite in polarity to that induced on said airborne particles by said germicidal agent, for collecting and removing charged airborne particles from said air stream;

whereby bacteria and other germ agents are neutralized by said germicidal agent, and airborne particles are collected from said air stream as it passes through said purifying device.

2. The apparatus according to claim 1 where said germicidal agent is FDA CRMCS No. 1R0013919.

3. The apparatus according to claim 1 wherein said collecting means comprises a stack of spaced, parallel metallic plates connected to a voltage source through a transformer and separated by a dielectric wafer.

4. The apparatus according to claim 3 wherein said transformer is of such size as to effect a voltage from the secondary winding of at least 4000 volts.

5. The apparatus according to claim 4 wherein said fan and the dimension of said enclosure are of such size as to be capable of generating an air flow of 45–50 cubic feet per minute.

* * * * *